United States Patent [19]

Murib

[11] Patent Number: 4,552,860

[45] Date of Patent: Nov. 12, 1985

[54] CATALYST FOR THE PREPARATION OF UNSATURATED ALDEHYDES AND CARBOXYLIC ACIDS

[75] Inventor: Jawad H. Murib, Cincinnati, Ohio

[73] Assignee: National Distillers and Chemical Corporation, New York, N.Y.

[21] Appl. No.: 653,817

[22] Filed: Sep. 21, 1984

Related U.S. Application Data

[60] Division of Ser. No. 378,294, May 14, 1982, Pat. No. 4,499,301, which is a continuation of Ser. No. 31,819, Apr. 20, 1979, abandoned.

[51] Int. Cl.$^4$ .................. B01J 23/44; B01J 23/48; B01J 23/72; B01J 21/06
[52] U.S. Cl. .................. 502/242; 502/309; 502/333; 502/339; 502/345; 502/346; 502/347; 502/348
[58] Field of Search ............... 502/242, 309, 333, 339, 502/345, 346, 347, 348

[56] References Cited

U.S. PATENT DOCUMENTS 3,927,111  12/1975  Robinson .................. 562/546

FOREIGN PATENT DOCUMENTS 47-6606  2/1972  Japan .................. 562/546
1170663  11/1969  United Kingdom .................. 502/348

*Primary Examiner*—W. J. Shine
*Attorney, Agent, or Firm*—Kenneth D. Tremain

[57] ABSTRACT

Catalyst for use in a vapor phase process for the preparation of unsaturated aldehydes, carboxylic acids and mixtures thereof which comprises a noble metal promoted by a solid acid consisting of mixed metal oxides.

19 Claims, No Drawings

CATALYST FOR THE PREPARATION OF UNSATURATED ALDEHYDES AND CARBOXYLIC ACIDS

This is a divisional of copending application Ser. No. 378,294, filed on May 14, 1982, now U.S. Pat. No. 4,499,301, which is a continuation of application Ser. No. 031,819 filed Apr. 20, 1979, now abandoned.

BACKGROUND OF THE INVENTION

The present invention relates to a low temperature vapor phase process for the selective preparation of acrolein, acrylic acid and mixtures thereof which comprises contacting propylene, water and oxygen with a solid catalyst comprising a catalytically effective amount of noble metal such as palladium promoted by a solid acid consisting of mixed metal oxides, such as a mixture of molybdenum and titanium oxides.

Acrolein and acrylic acid and methacrolein and methacrylic acid are very important chemicals and are particularly useful in the preparation of a variety of commercial products, including plastic sheet and molding powder for signs, emulsion polymers for water-based paint formulations, paper coating, and many other such applications.

A number of processes have been proposed for the preparation of these materials and are well-known in the art. See, for example, "Encyclopedia of Chemical Technology", Second Edition, Kirk-Othmer, Vol. 1, pages 293-295. Also, Chapter 10 of "Propylene and its Industrial Derivatives", by E. G. Handcock, published by John Wiley, New York, 1973.

In general, the preparation of acrolein and/or acrylic acid from propylene is a catalytic oxidation process wherein the catalyst is the important feature of the invention. Thus, U.S. Pat. No. 2,941,007 discloses a process for the production of acrolein from propylene by catalytic oxidation using a catalyst consisting of bismuth molybdate and bismuth phosphomolybdate. U.S. Pat. Nos. 3,435,069 and 3,595,911 show the catalytic oxidation of propylene or acrolein to acrylic acid using a catalyst consisting of a mixture of an oxide of molybdenum and an oxide of titanium and antimony, molybdenum and titanium oxides, respectively. These processes are not desirable however, since they must be operated at relatively high temperatures above about 250° C., and preferably about 350° C. As is shown hereinbelow in Example 3, a catalyst composition containing only oxides of molybdenum and titanium does not produce acrolein or acrylic acid when propylene is oxidized at, say, 152° C. Thus, a need still exists for processes which are operable at relatively low temperatures, such as in the range of about 100° C.–250° C. and which are selective to acrolein and/or acrylic acid.

U.S. Pat. No. 3,792,086 (A) describes such a low temperature process employing a catalyst composition containing phosphoric acid and palladium metal in the preparation of acrylic or methacrylic acids by the vapor phase oxidation of propylene or isobutylene, respectively. A number of U.S. patents directed to the preparation of such products are noted therein. U.S. Pat. No. 3,947,495 (B) shows an improved catalyst composition containing a sulfur modifier, patents A and B being hereby incorporated by reference. These processes while useful to produce acrylic acid from propylene are not useful however, for the selective conversion of propylene to acrolein. Thus, for instance, Examples 1-10 in U.S. Pat. No. 3,792,086 produce only a small amount of acrolein relative to acrylic acid, e.g., an acrylic acid to acrolein mole ratio of from about 5.5/1 to 30/1. A similar run as shown hereinbelow provides an acrylic acid to acrolein mole ratio of about 1/5, thereby significantly changing the selectivity of the propylene oxidation process.

It is among the objects of the present invention to provide a new and improved low temperature process for the selective preparation of acrolein, acrylic acid and mixtures thereof from propylene by a direct and efficient vapor phase process.

It is a further object of the invention to provide a new catalyst composition and a method for making the catalyst.

Other objects and advantages of the invention will be apparent from the following description.

SUMMARY OF THE INVENTION

It has been found that acrolein, acrylic acid and mixtures thereof may be selectively prepared by a direct and efficient low temperature vapor phase process comprising contacting a gaseous mixture of propylene, water and oxygen at an elevated temperature up to about 250° C. with a solid catalyst comprising a catalytically effective amount of noble metal promoted by a solid acid consisting of mixed metal oxides.

A further advantage of the process according to the present invention is that propylene may be converted directly to acrylic acid if the reaction conditions are chosen appropriately; in this connection, the commercial investment is considerably lower for a single-step process than for a two-step process.

The following description of the preferred forms of the invention will relate principally to the oxidation of propylene to acrolein and acrylic acid. It will be understood, however, that the instant process is equally applicable to the vapor phase oxidation of isobutylene to methacrolein and methacrylic acid, and that such latter embodiment is also embraced within the scope of the present invention. Also contemplated is the use of other olefins to produce the corresponding unsaturated aldehydes and carboxylic acids.

The process is generally carried out at low elevated temperatures, e.g., up to about 250° C., employing a solid catalyst contact system, such as a system utilizing a fixed, moving or fluidized catalyst bed.

DESCRIPTION OF THE PREFERRED EMBODIMENTS

The propylene reacted in the present process may be used in pure form or in diluted form, such as, for example, in the form of a mixture containing up to about 50 mole percent of diluents, usually inert hydrocarbons, e.g., methane, ethane, propane, and butane.

The oxygen feed may similarly be pure oxygen gas or, alternatively, an oxygen-containing gas mixture such as air or air enriched with oxygen. In addition to these materials the oxygen may contain other inert diluents such as carbon dioxide, nitrogen, and the like.

While stoichiometric proportions of the olefin and oxygen reactants, viz., 1.5 moles of oxygen per mole of propylene or isobutylene, may be utilized in the vapor phase process hereof, such compositions are within the flammable range. On the other hand, it may be preferred to operate outside flammable ratios and to use reaction mixtures in which either the oxygen or the olefin is the limiting reactant. Generally, mixtures are employed in which oxygen is incorporated in amounts of from about 1 to 99 mole percent, in admixture with from about 1 to 99 mole percent of the olefin; and, preferably, up to about 60, and desirably 5 to 50 mole percent of water vapor moderator. Obviously, when inert diluents are present in the reaction mixture, e.g., when the oxygen is added in the form of air, the proportions of the several reactants are correspondingly modified. Thus, propylene may be present in amounts of as low as 5 mole percent when the oxygen is introduced as air. The molar ratio of water to propylene may range between 0.1-20 to 1.0.

It is an important feature of the invention that a protonated material, such as water or alcohol vapor, be incorporated in the reaction mixture. The vapor may be added to the gaseous feed mixture by bubbling the gaseous olefin and/or oxygen streams through liquid water or alcohol. Alternatively, water or alcohol may be separately vaporized, as by flashing, and metered into the reaction zone. In the case of alcohol, esters of acrylic or methacrylic acid are produced depending on whether propylene or isobutylene is used.

The catalyst composition comprises a catalytically effective amount of noble metal, preferably palladium, promoted by a solid acid consisting of mixed metal oxides suitably supported on a conventional catalyst carrier such as, for example, alumina, silica, silicon carbide, titania, zirconia, zeolites, and the like. Silica or alumina is preferably utilized as the catalyst carrier in the process hereof because of its demonstrated effectiveness. The catalyst particle size, e.g., silica carrier, can vary over wide limits. A preferred form is an extrudate and generally has a specific surface area of about 50 to 500 square meters per gram ($m^2/g$) and is preferably about 100-300 $m^2/g$.

The noble metal is preferably selected from the group consisting of palladium, gold and silver. Copper may also be used. A preferred composition contains palladium and gold. The total amount of these metals, by weight of the total catalyst composition, is generally about 0.1 to 5%, and preferably about 0.5 to 2.0%.

The solid acid promoter is a mixture of metal oxides which exhibits acidic properties. For example, $MoO_3$-$TiO_2$, $TiO_2$-$ZnO$, $WO_3$-$P_2O_5$, $TiO_2$-$V_2O_5$, $MoO_3$-$SiO_2$ and the like are active promoter pairs for the noble metal. Particularly preferred is a mixture of molybdenum and titanium oxides. The relative amounts of mixed metals in the solid acid promoter is preferably such that the atomic ratios of the mixed metals imparts maximum acidic character to the catalyst system. For example, in the case of mixed titanium and molybdenum oxides, the atomic ratio of $Mo/(Ti+Mo)$ is between about 0.4 and 0.8. The total amount of solid acid is not critical, but is generally, in weight %, about 1 to about 60% of the total catalyst composition, and preferably about 10 to 25%.

The catalyst composition may be prepared by known techniques; however, it is highly preferred that the following procedure be employed:

Step (a)—treating the carrier (spraying, applying solutions or otherwise depositing on the carrier) with a solution containing the soluble salts of the solid acid promoter and heating to dryness; Step (b)—calcining the treated carrier in air at a temperature up to about 1,000° C., preferably about 400° C. to 600° C.; Step (c)—treating, as in Step (a), the calcined carrier with a solution of the noble metal(s) and heating to dryness; and Step (d)—contacting the treated carrier with a reducing agent, e.g., hydrogen, alkaline formaldehyde, metal borohydride, hydrazine, and the like, to reduce the noble metal to the metallic state under conditions whereby the solid acid promoter is not reduced, e.g., treating with hydrogen below the temperature at which the solid acid would be reduced.

This reaction is conducted in the vapor phase and is relatively simple and efficient since no moving parts are required in the processing equipment. Product separation is simplified and the reaction product can be separated from the reaction mixture by techniques such as distillation or solvent extraction. Further, vapor phase reactions generally permit continuous operation and do not necessitate the use of expensive, volatile solvents, as in liquid phase systems.

In carrying out the process, it may be conducted at atmospheric or elevated pressures, e.g., up to about 300 pounds per square inch gauge (psig), or higher. Higher pressures are not normally employed because of increased equipment and operating costs. It is generally preferred to carry out the process under atmospheric pressure or at pressures only slightly in excess of atmospheric, e.g., up to about 50 psig, and most preferably up to about 20 or 30 psig, e.g., 10 psig.

The reaction temperature employed in the process may be varied over a relatively wide range and, for example, temperatures of as high as about 250° C. are suitable. It is preferred to maintain the reaction temperature at about 100°-250° C., and most preferably about 125°-225° C., e.g., 152° C.

It is an important feature of the invention that the reaction temperature and the contact time of the reaction stream and the catalyst be correlated to control the selectivity of the reaction. Thus, the formation of acrolein is favored by lower reaction temperatures and shorter contact times, the converse being true for the formation of acrylic acid. When maximum conversion to acrylic acid is desired, it is advantageous to recycle the formed acrolein. The recycled acrolein can be combined with a recycle of unreacted olefin. To favor the formation of acrolein from propylene, a temperature range of about 100°-175° C., preferably about 125°-160° C., and a contact time of about 0.1-20 seconds, preferably 1-10 seconds and most preferably 1-5 seconds is desirably employed. Contact times of up to about 60 seconds, or higher, may be employed, e.g., 5-60 seconds, preferably 10-40 seconds, and this will favor the formation of acrylic acid, as will higher temperatures, such as about 150°-250° C., preferably 175°-250° C.

After the gaseous reaction mixture contacts the catalyst composition, the exhaust gases are cooled and the products separated by conventional techniques, e.g., distillation, solvent extraction, and the like. Unreacted feed material separated from the recovered effluent mixture may thereafter be recovered and recycled for further reaction.

The following examples are given for purposes of illustration only and are not to be considered as constituting a limitation on the present invention.

As employed herein, % Conversion, % Selectivity and Catalyst Utility are defined as follows:

$$\% \text{ Conversion} = \frac{\text{No. of moles feed olefin consumed} \times 100}{\text{No. of moles feed olefin}}$$

$$\% \text{ Selectivity} = \frac{\text{No. of moles specified component formed} \times 100}{\text{No. of moles of specified reactant consumed}}$$

The term "Catalyst Utility" means millimoles (mmoles) produced/liter catalyst/hour.

EXAMPLE 1

Preparation of Catalyst

Step 1: Deposition of metal oxides on the catalyst carrier 200 grams (g.) of extruded silica gel ⅛ inch diameter×⅛-¼ inch long having a surface area of about 200 m²/g was placed in a 2-liter beaker, treated with 270 milliliters (ml.) of an aqueous solution containing 39.52 g. $TiCl_4$, 47.62 g. $H_2MoO_4$ (85% purity) and 97 g. HCl (36 wt. %). The mixture was then heated to dryness with continuous mixing on a hot plate. The resulting extrudates were calcined in air at 500° C. for 12 hours.

Step 2: Deposition of noble metals on the catalyst carrier 17 g. (30 ml.) of the calcined carrier was loaded with, by weight of the catalyst, about 1.3% Pd and 0.5% Au, by treatment with 20 ml. of an aqueous solution containing 0.31 g. $PdCl_2$, 0.18 g. $HAuCl_4 \cdot 3H_2O$ and 0.13 g. HCl (36 wt. %). The mixture was heated to dryness in an open rotating dish with a stream of hot air. It was then placed in a tubular reactor and heated with a nitrogen stream at 200° C. for two hours, followed by a stream of hydrogen at 240° C. for four hours.

EXAMPLE 2

Preparation of Acrolein and Acrylic Acid

A 30 ml. pyrex glass reactor, 12 centimeters (cm.)×2.5 cm. (outside diameter) provided with a thermowell (0.8 cm. outside diameter (O.D.) extending the entire length of the reactor, was attached to a preheating zone (1.2 cm.×15 cm.) and a capillary exit tube (0.1 cm.×10 cm.) to permit rapid quenching. The reactor was packed with 30 ml. of the catalyst prepared in Example 1 and heated in an oil bath at about 152° C. A gaseous stream having the composition 5.1 mole % propylene, 15.2 mole % oxygen, 30.3 mole % nitrogen and 49.4 mole % steam was passed through the heated catalyst at a contact time of about three seconds. The reactor effluent was passed through a water bubbler containing 50 ml. of deionized water cooled with ice. Analysis of the resulting aqueous solution and of the vent gases by gas chromatography showed formation of:

|  | Catalyst Utility (Mmoles/liter cat./hr.) |
| --- | --- |
| Acrolein | 106.0 |
| Acrylic | 23.2 |
| Acetone | 20.0 |
| $CO_2$ | 13.3 |

The oxidation of propylene resulted in 84.8% selectivity to acrylics (69.6% to acrolein and 15.2% to acrylic acid) based on reacted propylene and a % Conversion of propylene of 8.6% per single pass.

EXAMPLE 3

Comparative Example Using Mixed $TiO_2$-$MoO_3$ Without Pd and Au

Example 2 was repeated using 30 ml. of the carrier prepared in Step 1 of Example 1. The feed, consisting of 4.8 mole % propylene, 14.5 mole % oxygen, 28.9 mole % nitrogen and 51.8 mole % steam, was fed to the heated reactor maintained at 152° C. at 2.8 seconds contact time. Combustion predominated and analysis of the products showed the presence of small amounts of isopropanol and acetone with no evidence of acrolein or acrylic acid.

This result shows that the oxidation to acrolein and acrylic acid is effected by the combination of Pd-Au and molybdenum and titanium oxides and, in the absence of Pd-Au, combustion occurs.

EXAMPLE 4

Preparation of Acrylic Acid from Acrolein

Example 2 was repeated except that the feed consisting of 3.9 mole % acrolein, 11.4 mole % oxygen, 38.9 mole % steam and 45.8 mole % nitrogen was passed through the heated reactor (152° C.) at 2.9 seconds contact time. Titrimetric analysis coupled with gas chromatography showed that acrylic acid was produced at a Catalyst Utility of 138.5 mmoles/liter cat./hr. at 73.5% selectivity based on reacted acrolein and a % Conversion of acrolein of 17% per single pass.

While the invention has been directed to propylene and acrolein and acrylic acid it will be understood that the disclosed process is applicable to the preparation of other corresponding unsaturated aldehydes, carboxylic acids and mixtures thereof from olefins and that such other embodiments are, therefore, also embraced within the scope of the present invention.

By the term "olefin" as used herein and in the appended claims is meant the open-chain as well as cyclic olefins. Among the many olefinic compounds which may be utilized in accordance with the process of the invention, the following compounds are illustrative: propylene, butene-2, isobutylene, etc. This invention is directed particularly to the oxidation of the lower olefins (3 to 4 carbon atoms), but higher olefins containing, e.g., $C_5$–$C_8$ atoms, may also be utilized. The process of the invention is applicable to individual olefins as well as to mixtures of olefins and also to mixtures of olefins with the corresponding or other saturated organic compounds.

The process of this invention is particularly adapted to the conversion of propylene to acrolein and/or acrylic acid and of isobutylene to methacrolein and/or methacrylic acid.

It will be apparent that many changes and modifications of the several features described herein may be made without departing from the spirit and scope of the invention. It is therefore apparent that the foregoing description is by way of illustration of the invention rather than limitation of the invention.

We claim:

1. A method for preparing a catalyst useful for the oxidation of propylene to acrolein, acrylic acid, and mixtures thereof wherein the catalyst consists essentially of a metal selected from the group consisting of palladium, gold, silver and copper and a solid acid promoter consisting of a mixture of molybdenum trioxide and titanium dioxide supported on a carrier which comprises:

Step (a) treating a carrier with a solution containing soluble salts of the solid acid promoter and heating to dryness;

Step (b) calcining the treated carrier in air at a temperature of about 400° C. to 600° C.;

Step (c) treating the calcined carrier with a solution of a compound of said metal and heating to dryness; and Step (d) contacting the treated carrier with a reducing agent to reduce said metal to the metallic state under conditions whereby the solid acid is not reduced to the metallic state.

2. A solid catalyst composition prepared in accordance with claim 1.

3. A solid catalyst composition useful for the oxidation of olefins to form corresponding unsaturated aldehydes and carboxylic acids and mixtures thereof which comprises a catalytically effective amount of a metal selected from the group consisting of palladium, gold, silver and copper promoted by a solid acid consisting of a mixture of molybdenum trioxide and titanium dioxide.

4. A method as in claim 1 in which said metal is a mixture of palladium and gold.

5. A method as in claim 4 in which said promoter is a mixture of said molybdenum and titanium oxides wherein the atomic ratio of Mo/(Ti+Mo) is between about 0.4 and 0.8.

6. A method as in claim 5 in which said carrier is silica or alumina.

7. A method as in claim 6 in which, by weight of the total catalyst composition, the total amount of metal is about 0.1% to 5% and the total amount of promoter is about 1% to 60%.

8. A solid catalyst as in claim 3 in which said metal is a mixture of palladium and gold.

9. A solid catalyst as in claim 8 in which said promoter is a mixture of said molybdenum and titanium oxides wherein the atomic ratio of Mo/(Ti+Mo) is between about 0.4 and 0.8.

10. A solid catalyst as in claim 9 in which said carrier is silica or alumina.

11. A solid catalyst as in claim 10 in which, by weight of the total catalyst composition, the total amount of metal is about 0.1% to 5% and the total amount of promoter is about 1% to 60%.

12. A method as in claim 1 in which said metal is palladium.

13. A method as in claim 1 in which said metal is gold.

14. A method as in claim 1 in which said metal is silver.

15. A method as in claim 1 in which said metal is copper.

16. A catalyst as in claim 3 in which said metal is palladium.

17. A catalyst as in claim 3 in which said metal is gold.

18. A catalyst as in claim 3 in which said metal is silver.

19. A catalyst as in claim 3 in which said metal is copper.

* * * * *